United States Patent [19]

Kraemer et al.

[11] 4,208,309

[45] Jun. 17, 1980

[54] PEARL POLYMER CONTAINING HOLLOW PEARLS

[75] Inventors: Dieter Kraemer, Mainz; Hermann Plainer; Waldemar Schleier, both of Darmstadt, all of Fed. Rep. of Germany

[73] Assignee: Röhm GmbH, Darmstadt, Fed. Rep. of Germany

[21] Appl. No.: 49,438

[22] Filed: Jun. 18, 1979

Related U.S. Application Data

[62] Division of Ser. No. 905,892, May 15, 1978.

[30] Foreign Application Priority Data

May 20, 1977 [DE] Fed. Rep. of Germany ....... 2722751

[51] Int. Cl.² .............................................. C08J 9/00
[52] U.S. Cl. ........................................ 260/8; 195/62; 521/25; 521/34; 521/38; 521/56; 521/149; 521/150
[58] Field of Search ................. 260/8; 521/29, 34, 38, 521/56, 149, 150; 195/62

[56] References Cited

U.S. PATENT DOCUMENTS

| | | | |
|---|---|---|---|
| 3,886,125 | 5/1975 | Chromecek | 260/79.7 |
| 3,925,267 | 12/1975 | Coupek et al. | 260/2.5 R |
| 3,948,866 | 4/1976 | Pennwiss et al. | 260/79.3 MU |
| 3,957,741 | 5/1976 | Rembaum et al. | 260/2.5 B |
| 4,046,720 | 9/1977 | Rembaum et al. | 526/312 |
| 4,070,348 | 1/1978 | Kraemer | 260/2.5 B |

*Primary Examiner*—Morton Foelak
*Attorney, Agent, or Firm*—Curtis, Morris & Safford

[57] ABSTRACT

What is disclosed is a pearl polymer product, a method of making the same, and the use thereof as a carrier for biologically active materials, said product being composed of hollow pearl particles having a diameter from 5 to 1000 microns and consisting of a cross-linked polymer which is a cross-linked homopolymer or copolymer comprising at least one member selected from the group consisting of acrylamide, methacrylamide, methylene-bis-acrylamide and methylene-bis-methacrylamide, said polymer containing at least 5 percent by weight of a monomer having at least two carbon-carbon double bonds which are activated by a neighboring phenyl group or carbonyl group, said polymer further being of a composition such that $x+3y \geq 40$, where x is the percent by weight in the polymer of acrylamide and methacrylamide and y is the percent by weight in the polymer of methylene-bis-acrylamide and methylene-bis-methacrylamide.

3 Claims, No Drawings

PEARL POLYMER CONTAINING HOLLOW PEARLS

This is a division of application Ser. No. 905,892, filed May 15, 1978.

The present invention relates to pearl polymers which are cross-linked homopolymers or copolymers comprising at least one member selected from the group consisting of acrylamide, methacrylamide, methylene-bis-acrylamide, and methylene-bis-methacrylamide, optionally together with further free-radical polymerizable comonomers, and to methods of making and using such polymers.

Pearl polymers of this composition which contain as comonomers unsaturated compounds having groups which are reactive with hydroxy groups or amino groups are used as carriers for enzymes and other biologically active materials. The reaction with these active agents remains limited to the surface of the pearl polymers or, at best, to a layer lying near the surface, to the extent that the layer can be reached by diffusion. The same is true for the use of pearl polymers as adsorption agents or as ion exchangers. In all cases the binding capacity depends on the total surface of the pearl polymer employed. The surface available per unit weight is inversely proportional to the diameter of the pearls. In order to increase the active surface per unit weight, the diameter of the pearls must be decreased. The preparation of spherical particles less than one micron in diameter is, to be sure, technically possible by emulsion polymerization. However, the isolation and handling of such small particles is difficult. Practically it is not possible to arrange particles of this order of magnitude into a layer and to let it be permeated by a reaction medium. Good handling, filterability, and permeability to streaming are first present in spherical particles of at least five microns, particularly in the region from 50 to 1000 microns. However, the surface/volume ratio is not optimum at this particle size; a considerable portion of the reactive groups which are optionally polymerized into the structure are so far removed from the surface that they do not react.

An object of the invention was to prepare pearl polymers having a particle diameter of 5 to 1000 microns wherein the bonding capacity or reaction capacity per unit weight is improved in comparison with customary pearl polymers. This problem is solved according to the invention by means of a pearl polymer containing hollow pearls having a diameter from 5 to 1000 microns and which is a cross-linked homopolymer or copolymer comprising at least one member selected from the group consisting of acrylamide, methacrylamide, methylene-bis-acrylamide, and methylene-bis-methacrylamide, optionally together with further free-radically polymerizable comonomers. Said polymer comprises at least 5 percent by weight of units of a monomer having at least two carbon-carbon double bonds activated by a neighboring phenyl group of carbonyl group. The new pearl polymers have a composition agreeing with the formula $x + 3y \geq 40$, wherein x is the percent by weight therein of acrylamide and/or methacrylamide and y is the percent by weight of methylene-bis-acrylamide and/or methylene-bis-metacrylamide. The cavity in the polymer pearls is in the general at least 20 percent by volume of the pearls, preferably at least 50 volume percent, and can amount to more than 90 volume percent. The cavity can be filled with air or with liquids, for example also with solutions of active agents or of dyes. In the pearl polymers according to the invention, the polymer is present in a spherical shell. The shell structure can best be observed under a microscope if the hollow pearls are broken by compression or rubbing. The increased bonding capacity of the hollow pearls, in comparison with solid pearls of a similar composition, which is illustrated by the bonding of the enzyme ribonuclease onto a copolymer containing an oxirane group, for example.

|  | Product according to the invention | Conventional Compact Pearl Polymer |
|---|---|---|
| Composition | 50 pbw methylene-bis-methacrylamide<br>25 pbw acrylamide<br>25 pbw glycidyl acrylate | 0.6 pbw methylene-bis-methacrylamide<br>74.4 pbw acrylamide<br>25 pbw glycidyl acrylate |
| Swelling in water at 25° C. (in parts by volume per one part by volume of the unswollen material) | 3.1 | 10 |
| Epoxy-oxygen content | 1.29 percent by weight | 1.38 percent by weight |
| RNase-activity* on 1 g of pearl polymer (moist weight) | 69 U/g | 15–20 U/g |
|  | (See example 1 for a definition of this activity unit) | |

*Activity determination on RNA yeast (Boehringer, Mannheim) as the substrate: pH - value = 7.5; 37° C. Incubation batch: 20 ml. Substrate solution (4% RNA, Na-salt) and 0.5–2.0 g of carrier-bound RN-ase.

Analytical demonstration of the oxirane groups was carried out according to Axen [L. Sundberg, J. Porath, Journal of Chromatography, 90, 97 (1974)] in such a way that not only the oxirane ring groups present on the pearl surface, but also such groups in the interior of the polymer matrix, were included. Although also in this case only a portion of the oxirane groups present in the polymer are determined, both polymers agree substantially in the content of groups detectable this way. However, the bonding capacity toward ribonuclease is higher by a factor of 3 to 4 in the hollow pearls.

The formation of the pearl polymers as hollow pearls is dependent both on the polymer composition as well as on the method of preparation. For preparing hollow pearls, a solution containing 10 to 80 percent of the monomers to be employed, preferably 20 to 40 percent, by weight of the solution, and containing a solvent in which the monomer or monomers are soluble and in which the polymer formed is insoluble, is suspended in the form of droplets in an organic liquid which is immiscible with the monomer solution or is only of limited miscibility therewith, and polymerization of the monomer is inititated by means of a free radical-forming initiator.

Although the invention is not to be based on a specific theory, the formation of hollow pearls can be attributed to a separation, within each droplet of monomer solution, of the strongly crossed-linked polymer from the monomer solution after even only slight conversion and to the inclusion of the monomer solution in its interior. In the further course of the polymerization, newly-forming polymer molecules attach to the polymer shell initially formed until, finally, only the solvent in which the monomers were originally dissolved is to be found in the interior of the droplet. Separation of the polymer presupposes a strong incompatibility with the monomer solution. This incompatibility depends, on the one hand, on the cross-linking brought about by the presence of methylene-bis-acrylamide and/or methylene-bis-methacrylamide and, on the other hand, on the cross-linking by way of hydrogen bridges of the amide groups. The effect of the methylene-bis-acrylamide and/or -methacrylamide on incompatibility has proved to be about three times as strong as the effect of acrylamide and/or of methacrylamide, so that one part by weight of methylene-bis-acrylamide and/or -methacrylamide produces incompatibility to the same degree as do three parts by weight of acrylamide or methacrylamide. The sum of x+3y, which should be at least 40, can reach a maximum value of 300 and preferably is from 120 to 200. Optionally, x or y may take a zero value. If methylene-bis-acrylamide and -methacrylamide are not present in the polymer, that is y=0, then at least five percent by weight of the total weight of the monomers must be other monomers having at least two carbon-carbon double bonds activated by neighboring phenyl groups or carbonyl groups, which monomers are present as a cross-linking agent. Example of these cross-linking agents are the diacrylates and dimethacrylates of glycols or the like, monomers known as cross-linking agents and having two or more acrylic or methacrylic functional groups, and divinylbenzene. With compounds with carbon-carbon double bonds which are not activated in the manner indicated, for example compounds having allyl groups, the required density of cross-linking can be reached only with difficulty.

As a rule the pearl polymers according to the invention do not only comprise acrylamide or methacrylamide or the corresponding methylene-bis-amides, but contain further comonomers the nature of which is largely determined by the intended end use of the polymer. The comonomers must be more soluble in the monomer solution than in the organic liquid in which the monomer solution droplets are suspended during polymerization. This requirement is primarily fulfilled by strongly polar monomers, such as acrylic acid or methacrylic acid or their salts.

A particularly important group of comonomers are those which have a group reactive with primary amino groups or hydroxy groups of biologically-active substances to form a covalent bond. These materials can be free-radically polymerizable monomers having an oxirane group, a carboxylic acid anhydride group, a carboxylic acid chloride group, a carboxylic acid azide group, a carboxylic acid phenyl ester group, or a group of the formula

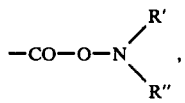

wherein R' and R" taken alone are the same or different alkyl or acyl grups and wherein R' and R" taken together may be bound to the N atom to form a heterocyclic ring. Preferred monomers having an oxirane group are glycidyl acrylates or glycidyl methacrylates or vinyl glycidyl ethers or allyl glycidyl ethers. Pearl polymers formed in this way, particularly those comprising 10-15 percent by weight of acrylamide or methacrylamide, 20-60 percent by weight of methylene-bis-acrylamide or -methacrylamide, and 10 to 70 percent by weight of glycidyl -acrylate, -methacrylate, -vinyl ether, and/or -allyl ether have proved to be outstanding as carriers for biologically active substances, in particular enzymes.

Pearl polymers comprising comonomers having acidic or basic or salt-like groups are suitable as ion exchanges and, in contrast to the known ion exchange resins, have a high binding capacity toward organic cations or anions of considerable molecular size. Such cid exchange resins can contain units of unsaturated carboxylic acids such as acrylic acid or methacrylic acid, itaconic acid, maleic acid, or fumaric acid, or their alkali metal or ammonium salts. Cations exchange resins can contain, for example, dialkylaminoalkyl esters of acrylic acid or methacrylic acid or the salts or quaternization products thereof as comonomers. Pearl polymers free of comonomers in addition to acrylamide or methacrylamide or the corresponding methylene-bis-amides can be used as adsorption agents in chromatographic methods and similar purposes. The hollow pearls according to the invention are in every case preferably used with aqueous media. The solvents present in thecavity from preparation are quickly exchanged for water in aqueous media.

The preparation of the pearl polymer according to the present invention takes place according to a suspension polymerization process proceeding in an organic phase, which process is also designated as "reverse pearl polymerization". In this process, a polar monomer phase is suspended in the form of droplets in a non-polar organic liquid. The monomer phase may not be miscible with the non-polar organic fluid, or at most may be only limitedly miscible therewith, so that two separate phases can be formed. The phase ratio between the suspended monomer phase and the organic liquid can be between 1:4 and 4:1 (in parts by volume), for example.

For maintenance of the desired condition of subdivision in which the monomer phase is present in droplets of a diameter from about 5 to 1000 microns, a dispersing agent behaving like a surface active agent or like a protective colloid is generally employed. The working method described in U.S. Pat. Nos. 3,948,866 and 4,070,348 and in German Patent Publication DT-OS No. 23 43 633, all incorporated herein by reference, is suitable for the process of the invention. In this method, a statistical copolymer, block copolymer, or graft copolymer which is soluble in the organic liquid is employed as the dispersing agent, said copolymer comprising from 60 to 98 mol percent of acrylic acid esters or methacrylic acid esters of alkanols having at least four carbon atoms or of vinyl esters of fatty acids containing at least four carbon atoms, and comprising polar water-soluble monomers as the balance. Preferred dispersing agents are statistical copolymers comprising 60 to 96 mol percent of alkyl esters of acrylic or of methacrylic acid having 4 to 18 carbon atoms in the alkyl portion and from 40 to 5 mol percent of an acid addition salt or quaternary ammonium salt of an aminoalkyl ester of acrylic acid or of methacrylic acid.

In the case of block copolymers or graft copolymers, the polar monomer units are only polymerized in a block or in the graft copolymer branches. For the selection of specifically suitable monomer components for the dispersing agent, as well as for a process for their preparation, reference is made to the aforementioned U.S. and German patents, particularly to U.S. Pat. No. 3,948,866.

The solvent component of the monomer phase is so chosen that the monomer or monomers are soluble therein and the polymer formed is insoluble therein. Further, the solution must be incompatible with the organic liquid serving as the suspension medium. To the extent monomers having groups which are reactive with water are present in the monomer phase, especially those monomers mentioned earlier as preferred for reaction with biologically active materials, the solvent must additionally be inert toward the monomers. Solvents which fulfill these requirements are, for example, formamide, monomethylformamide, dimethylformamide, or dimethylsulfoxide. Formamide is a preferred solvent and can be used alone or in mixtures also containing up to 50 percent by weight of monomethylformamide, dimethylformamide, or dimethylsulfoxide. As already explained above, the amount of the solvent in the suspended monomer phase influences the size of the cavity in the hollow pearls which are formed. After complete conversion of the monomers, only the solvent remains in the enclosed cavity. If the monomer phase contains 10 percent by weight of monomers and 90 percent by weight of solvent, then polymer pearls are formed with a cavity which comprises about 90 percent of the volume of the sphere. The cavity naturally does not correspond exactly to the percent by weight of the solvent since the density difference between the solvent and the monomers, or the polymer formed therefrom, must be taken into consideration. Further deviations from the cavity volumes estimated in advance can result from a limited mutual solubility of the phases. There is an optimum in many cases at a concentration of the monomer phase between 20 and 40 percent by weight, because, on the one hand, the hollow pearls which are formed have an advantageous surface/volume ratio as a result of their shell structure and, on the other hand, they have a mechanical strength which is sufficient for use.

The non-polar liquid serving as the continuous polymerization medium generally comprises a gasoline hydrocarbon which optionally may be present in admixture with a chlorohydrocarbon, or comprises benzene, toluene, or xylene. For initiation of the polymerization, free radical forming initiators are employed in a manner known per se. It has not proved to be necessary to the polymerization process that the initiator only be soluble in one of the phases. As initiators, benzoyl peroxide, particularly in combination with dimethylaniline, tert.-butyl-perpivalate, azo-bis-isobutyronitrile, 4,4'-azobis-(4-cyanovalerianic acid), and the like are suitable, for example.

Further details of the polymerization and recovery process are evident from the following Examples, given by way of illustration.

EXAMPLE 1

A solution of
21 g of N,N'-methylene-bis-methacrylamide,
9 g of glycidyl methacrylate, and
0.6 g of dibenzoyl peroxide
in 120 g of formamide are distributed with stirring at 55° C. in an organic phase comprising
170 g of n-heptane,
110 g of perchloroethylene, and
0.1 g of a polymeric emulsifier (copolymer comprising 95 parts of n-butyl methacrylate and 5 parts of trimethylammonium-ethylmethacrylate-chloride)
present in a 1 liter round flask provided with a stirrer and reflux condenser. Polymerization is initiated by the addition of 0.6 g of dimethylaniline. The batch is stirred for four hours at 55° C.; the pearl polymer obtained is filtered off and washed with acetone. Subsequently it is dried for 12 hours in vacuum (20 mm Hg) at room temperature. Conversion: 97 percent. Under a microscope, translucent-milky hollow pearls of about 0.1 mm diameter can be recognized.

These hollow pearls are used as carriers for enzymes. Reactions, for example with RN-ase, were carried out as follows:

50 mg of ribonuclease-A (bovine pancreas, crystallized five times, purity=45 Kunitz units/mg, obtained from Serva as No. 34390) are dissolved in 2.0 ml of aqueous 0.2 M $Na_2HPO_4$ solution and are added to 250 mg of polymer pearls. The mixture is stirred well and left to stand at 23° C. for 72 hours. Then the pearls are washed four times with 50 ml portions of an aqueous 1 M NaCl solution and finally twice with 50 ml portions of a phosphate buffer (0.05 M, pH 7.5) which contains 0.02 percent of sodium azide. Yield: 1.01 g of moist pearls. Enzymatic activity (RNA-yeast as substrate) : 70 U/g of moist pearls. Activity determination: 500 mg of moist pearls and 20 ml of substrate solution (4 percent RNA-yeast-sodium salt, adjusted to pH 7.5): automatic titration which a pH-stat of phosphoric ester groups cleaved by hydrolysis with 0.5 N NaOH at pH 7.5 and at 37° C. with simultaneous registration of the amount of NaOH used with a stylus (Titrigraph, Type SBR 2, manufactured by Radiometer).

Unit activity =1 micromol of cleaved phosphoric ester bonds/minute, corresponding to 1 micromol of NaOH/minute (=6.67 Kunitz units)

Evaluation: corresponding to the initial velocity in the linear portion of the kinetic curve during the first four minutes of incubation.

EXAMPLE 2

A solution of
12 g of N,N'-methylene-bis-methacrylamide,
5.7 g of methacrylamide,
1 g of methacrylic acid,
6 g of glycidyl methacrylate,
6 g of allyl glycidyl ether, and
0.6 g of dibenzoylperoxide
in 79 g of formamide is distributed with stirring at 55° C. in an organic phase comprising
174 g of n-heptane
110 g of perchloroethylene
0.1 g of polymeric emulsifier (copolymer of 95 parts of n-butylmethacrylate and 5 parts of 2-trimethylammonium-ethylmethacrylate-chloride present in a 1 liter round flask provided with a stirrer and reflux condenser. Polymerization is initiated by addition of 0.6 g of dimethylaniline. The mixture is stirred for four hours at 55° C. and the pearl polymer obtained is filtered and washed with acetone. Subsequently, it is dried for 12 hours in vacuum (20 mm Hg) at room temperature.

Conversion: 86.6 percent. Under a microscope, translucent-milky hollow pearls of about 0.1 mm diameter are recognizable. The pearls have a cavity volume of 70 percent.

A reaction with RN-ase according to Example 1 gave 45.3 U/g.

EXAMPLE 3

Examples 1 and 2 are repeated with the difference that the following is used as a monomer solution:
- 79 g of formamide,
- 21 g of 2-hydroxyethyl methacrylate,
- 3 g of N,N'-methylene-bis-methacrylamide,
- 6 g of methacrylamide, and
- 0.6 g of tert.-butylperpivalate.

Polymerization and working up follow as previously.

Almost opaque white hollow pearls ("table tennis balls") of about 0.1 mm diameter are obtained. Yield: 100 percent.

EXAMPLE 4

Example 1 and 2 are repeated with the difference that the following is used as a monomer solution:
- 79 g of formamide,
- 50 g of methacrylamide,
- 15 g of ethylene glycol dimethacrylate, and
- 0.6 g of dibenzoylperoxide Polymerization and working-up follow as previously.

Fine transparent hollow pearls ("bubbles") are obtained. Conversion: 93%. Particle size: 0.05 mm.

EXAMPLE 5

A solution of
- 12 g of N,N'-methylene-bis-methacrylamide,
- 6 g of acrylamide,
- 6 g of glycidyl acrylate,
- 6 g of allyl glycidyl ether, and
- 0.6 g of dibenzoyl peroxide in 79 g of formamide is distributed with stirring at 55° C. in an organic phase comprising
- 174 g of n-heptane,
- 110 g of perchloroethylene, and
- 0.1 g of polymeric emulsifier (copolymer of 95 parts of n-butyl-methacrylate and 5 parts of 2-trimethylammonium ethylmethacrylate-chloride)

contained in a one liter round flask provided with a stirrer and reflux condenser. The polymerization is started by the addition of 6 g of dimethylaniline. The mixture is stirred for 8 hours at 55° C. The pearl polymer obtained is filtered off and washed several times with acetone. Subsequently it is dried for 12 hours in vacuum (20 mm Hg).

Milky to translucent pearls of about 0.05 mm diameter are obtained and reveal their shell character when crushed. Conversion: 91.5%.

EXAMPLE 6

Example 5 is repeated with the difference that the following monomer solution is employed:
- 77 g of formamide,
- 10 g of N,N'-methylene-bis-methacrylamide
- 7 g of N,N'-methylene-bis-acrylamide,
- 3 g of glycidyl methacrylate,
- 3 g of vinyl glydicyl ether, and
- 0.6 g of dibenzoyl peroxide.

Polymerization and working up are as before.

Opaque white hollow pearls of about 0.1 mm diameter are obtained. Conversion: 98%

EXAMPLE 7

Example 5 is repeated with the difference that the solvent in the monomer phase comprises 50 g of formamide and 27 g of dimethylformamide.

Loosely agglomerated hollow pearls of about 0.05 mm diameter are obtained; they separate into individual pearls under the influence of light pressure. Conversion: 85%.

EXAMPLE 8

200 mg immunoglobulin-G(Ig-G) are dissolved in 40 ml of phosphate buffer (pH 7.5, 0.1 M) and added to 1000 mg of polymer pearls according to Example 1. The mixture is allowed to stand for 72 hours at 23° C.

The pearls are washed as described in Example 1. Analysis of amino acids after hydrochloric acid hydrolysis showed that 125 mg of the immunoglobulin had been covalently linked to 1 g of polymer beads (dry weight).

What is claimed is:

1. A pearl polymer product having a protein bonded thereto, said pearl polymer product being composed of hollow pearl particles having a diameter from 5 to 1000 microns and consisting of a cross-linked copolymer comprising at least one member selected from the group consisting of acrylamide, methacrylamide, methylene-bis-acrylamide and methylene-bis-methacrylamide, and additionally comprising a free-radically-copolymerizable monomer having a group by which said copolymer is covalently bonded to a primary amino group or a hydroxy group of said protein, said polymer containing at least 5 percent by weight of a monomer having at least two carbon-carbon double bonds which are activated by a neighboring phenyl group or carbonyl group, said polymer further being of a composition such that $x + 3y \geq 40$, where x is the percent by weight in the polymer of acrylamide and methacrylamide and y is the percent by weight in the polymer of methylene-bis-acrylamide and methylene-bis-methacrylamide.

2. A pearl polymer product having a protein bonded thereto as in claim 1 wherein said protein is an enzyme.

3. A pearl polymer product having a protein bonded thereto as in claim 1 wherein said protein is an immunoglobulin.

* * * * *